(12) United States Patent
Berben et al.

(10) Patent No.: US 9,004,701 B2
(45) Date of Patent: Apr. 14, 2015

(54) LIGHT SOURCE UNIT AND PROJECTOR HAVING SUCH A LIGHT SOURCE UNIT

(75) Inventors: Dirk Berben, Herdecke (DE); Mathias Bruemmer, Wusterwitz (DE); Ulrich Hartwig, Berlin (DE); Nico Morgenbrod, Berlin (DE); Matthias Morkel, Berlin (DE)

(73) Assignee: Osram AG, Munich (DE)

( * ) Notice: Subject to any disclaimer, the term of this patent is extended or adjusted under 35 U.S.C. 154(b) by 282 days.

(21) Appl. No.: 13/578,834

(22) PCT Filed: Nov. 24, 2010

(86) PCT No.: PCT/EP2010/068122
§ 371 (c)(1),
(2), (4) Date: Aug. 14, 2012

(87) PCT Pub. No.: WO2011/098164
PCT Pub. Date: Aug. 18, 2011

(65) Prior Publication Data
US 2012/0316397 A1    Dec. 13, 2012

(30) Foreign Application Priority Data

Feb. 15, 2010    (DE) .......... 10 2010 001 942

(51) Int. Cl.
*G03B 21/28* (2006.01)
*A61B 18/22* (2006.01)
*G03B 21/16* (2006.01)
*H04N 9/31* (2006.01)
*G03B 21/20* (2006.01)
*A61B 18/00* (2006.01)

(52) U.S. Cl.
CPC ....... *A61B 18/22* (2013.01); *A61B 2018/00005* (2013.01); *G03B 21/16* (2013.01); *H04N 9/3161* (2013.01); *G03B 21/204* (2013.01)

(58) Field of Classification Search
CPC .......................... G02B 27/149; G02B 27/1053
USPC .......... 353/30, 31, 37, 38, 84, 85, 94, 98, 99; 362/84, 227, 231, 612, 621, 771, 800; 600/478, 109, 160, 178
See application file for complete search history.

(56) References Cited

U.S. PATENT DOCUMENTS

| | | | |
|---|---|---|---|
| 8,498,695 B2 * | 7/2013 | Westwick et al. ............. | 600/478 |
| 2005/0174768 A1 * | 8/2005 | Conner ......................... | 362/235 |
| 2005/0270775 A1 | 12/2005 | Harbers et al. | |

(Continued)

FOREIGN PATENT DOCUMENTS

| | | |
|---|---|---|
| DE | 102008011866 A1 | 9/2009 |
| EP | 1605199 A2 | 12/2005 |
| WO | 2009047683 A2 | 4/2009 |

*Primary Examiner* — Sultan Chowdhury

(57) ABSTRACT

A light source unit may include a cooling device; a luminescent substance; an excitation radiation source having a laser source; and an optical element arranged between the radiation source and the substance; wherein the cooling device constitutes a heat sink, wherein the substance is linked thermally to the heat sink; and wherein the optical element is designed as an integrating optical element and is coupled between the radiation source and the substance in such a manner that a part of the radiation emitted by the radiation source, entering in an acceptance angle range of the integrating optical element, is subjected to an internal reflection in the optical element before it exits the optical element and strikes the substance, and that a part of the radiation emitted by the substance enters the optical element and exits the optical element as effective radiation.

19 Claims, 3 Drawing Sheets

(56) References Cited

U.S. PATENT DOCUMENTS

| | | |
|---|---|---|
| 2007/0146639 A1 | 6/2007 | Conner |
| 2008/0030984 A1* | 2/2008 | Harbers et al. ............... 362/231 |
| 2009/0034284 A1 | 2/2009 | Li et al. |
| 2009/0040754 A1* | 2/2009 | Brukilacchio et al. ........ 362/228 |
| 2009/0284148 A1 | 11/2009 | Iwanaga |
| 2009/0284965 A1* | 11/2009 | Zheng et al. .................. 362/231 |
| 2009/0292168 A1* | 11/2009 | Farr .............................. 600/109 |
| 2013/0250546 A1* | 9/2013 | Hu et al. ......................... 362/84 |

* cited by examiner

LIGHT SOURCE UNIT AND PROJECTOR HAVING SUCH A LIGHT SOURCE UNIT

RELATED APPLICATIONS

The present application is a national stage entry according to 35 U.S.C. §371 of PCT application No.: PCT/EP2010/068122 filed on Nov. 24, 2010, which claims priority from German application No.: 10 2010 001 942.9 filed on Feb. 15, 2010.

TECHNICAL FIELD

Various embodiments relate to a light source unit having at least one cooling device, at least one luminescent substance, at least one excitation radiation source having a laser source and at least one optical element which is arranged between the at least one excitation radiation source and the at least one luminescent substance. Various embodiments further relate to a projector having such a light source unit and to a device for fiber coupling, e.g. an endoscope, having such a light source unit.

BACKGROUND

A generic light source unit and also a generic projector are known from US 2009/0284148 A1. In this case a multiplicity of segment regions is arranged on a transparent base material which is mounted such that it can be rotated and which in particular is formed on the basis of glass or resin. In at least two of these segment regions are applied layers of different luminescent substances which emit light within a predetermined wavelength range when they are excited by excitation light. The light source unit described therein furthermore includes an excitation light source for emitting light in the visible spectrum onto the luminescent substance layers.

A disadvantage of this known light source unit consists in the fact that the average luminance which can be achieved from a luminescent substance surface is comparatively low. Light source units having higher average luminances are desired in particular for use in projection applications and in devices for fiber coupling, in particular in endoscopes.

SUMMARY

Various embodiments further develop a light source unit in such a manner that a high luminance is made possible. Various embodiments provide a projector and a device for fiber coupling, e.g. an endoscope, having a corresponding light source unit.

Various embodiments are based on several elements of knowledge: The light source unit known from US 2009/0284148 A1 is difficult to cool on account of the transmittive modus operandi thereof because all the components concerned must be transparent owing to the principles involved. At the present time, inexpensive transparent materials are poor thermal conductors. Transparent materials having good thermal conductivity, such as for example sapphire or diamond, are too expensive for the present intended use. In the case of the aforementioned US publication, a fan is therefore employed for cooling, which fan is comparatively ineffective for cooling purposes. On account of this ineffective cooling in this known light source unit, the power density of the exciting radiation is greatly restricted and it is thus not possible to produce high luminances. By way of example, when such a light source unit is used in a projector the fan cooling results in an undesirably high noise level which is considered to be noise pollution.

In order to achieve particularly high luminances, a considerably more effective cooling device needs to be provided with regard to the Stokes shift occurring during the conversion and the absorption associated therewith. According to the invention, the cooling device is therefore designed in the first instance as a heat sink, whereby the at least one luminescent substance is linked thermally to this heat sink. In this situation, a heat sink is a device for the removal and subsequent dissipation of heat occurring to the surrounding area by means of a material having a high thermal conductivity, a liquid, through utilization of a phase transition, or thermoelectric converter. Preferred examples are aluminum heat sinks, liquid-cooled heat sinks, Peltier elements or heat pipes. As a result of the application of the luminescent substance on the heat sink it is possible to ensure excellent heat dissipation. The extremely high luminances are basically only made possible by this means. To this end, the heat sink must be manufactured from a non-transparent material in order to be able to accomplish such a high level of heat dissipation. Owing to the principles involved this therefore requires a construction which differs completely from the construction known from US2009/0284148 A1. According to the invention, in the case of a light source unit according to the invention the luminescent substance is therefore excited from one side and the effective radiation is delivered on the same side.

The invention is furthermore based on the knowledge that in the case of the known light source unit saturation effects already occur at certain positions of the luminescent substance while at other positions of the luminescent substance a considerable excitation potential still remains until saturation is reached. As high an average luminance as possible can therefore be achieved—given adequate cooling facilities for the luminescent substance—if the luminescent substance is excited in as homogeneous a manner as possible. According to the invention, this is achieved in that the optical element is designed as an integrating optical element, in other words as an optical element which effects a mixing or homogenization of the radiation entering the integrating optical element within an acceptance angle. According to the invention, this is achieved in that at least a part, preferably at least 50%, of the radiation emitted by the at least one excitation radiation source, entering in an acceptance angle range of the integrating optical element, is subjected to at least one internal reflection, preferably a plurality of internal reflections, in the integrating optical element before it—in other words this part—exits the integrating optical element again and strikes the at least one luminescent substance.

As a result of this measure, it becomes possible to minimize the difference between maximum and minimum excitation of the luminescent substance when considering the entire luminescent substance surface. An excitation of the luminescent substance up to the saturation range is therefore possible.

At least one part of the radiation emitted by the at least one luminescent substance enters the integrating optical element and exits the integrating optical element again as effective radiation according to the invention. Thanks to this dual use of the integrating optical element, it basically becomes possible for the cooling device—in contrast to the aforementioned US 2009/0284148 A1, in which the cooling device was designed as a fan—to be able to be designed in the present case as a heat sink, in particular as a non-transparent heat sink.

To summarize, it is therefore possible in the case of a light source unit according to the invention to operate the at least one luminescent substance to a high degree evenly over the entire luminescent substance surface close to the saturation limit. As a result of the fact that saturation effects are reliably prevented, the service life of the luminescent substance can be extended. Moreover, pointwise high luminescent substance temperatures which would result in losses in efficiency can likewise be avoided. Furthermore, undesired color coordinate shifts caused by temperature and radiation influences can be minimized in the case of a light source unit according to the invention.

A light source unit according to the invention, in particular additionally fitted with an optical system for fiber coupling, can be employed particularly advantageously in endoscopes and boroscopes.

By preference, the integrating optical element is furthermore designed in such a manner that at least a part of the radiation emitted by the at least one luminescent substance and entering the integrating optical element is subjected to at least one internal reflection in the integrating optical element before it exits the integrating optical element again.

This can be achieved by means of appropriate preparation of the boundary surfaces of the integrating optical element. These should accordingly be designed as reflective, in particular through use of a reflective coating, preferably however by means of total internal reflection, both for radiation from the excitation radiation source and also for radiation which is emitted by the at least one luminescent substance. As a result of this measure, the converted useful light or the excitation light diffused and reflected for an optimum white production is likewise mixed and homogenized in the integrating optical element.

With regard to a particularly preferred embodiment, the cross-section of the at least one integrating optical element is designed as not rotationally symmetrical, preferably angular, by particular preference rectangular. By this means, a particularly significant mixing of the radiation from the excitation radiation source is ensured, which means that a very homogeneous distribution of the intensity of the excitation radiation on the luminescent substance surface is achieved. This is advantageous in particular if the average optical excitation power density exceeds values of 2.5 $W/mm^2$. Thus, taking into consideration Stokes shift and conversion efficiency of the luminescent substance, optical power densities of the useful light greater than 1.6 $W/mm^2$ for white light and, associated therewith, high luminances in excess of 140 $cd/mm^2$ can be generated. Such values cannot be achieved using conventional LED technology in the near future. Without suitable homogenization the excitation power density may exceed the stated value many times over on a pointwise basis, which means that the aforementioned negative effects such as saturation of or damage to the luminescent substance result. Furthermore, color coordinate shifts are avoided as a result of a uniform illumination which can be achieved in this manner. Overall, a greater conversion efficiency is also obtained by the homogenization of the excitation radiation because said conversion efficiency drops disproportionately at a higher excitation power or higher temperature. An angular embodiment moreover has the advantage that the target area can thereby be optimally illuminated in a predefined height to width ratio, for example 16:9 or 4:4.

Particularly preferred furthermore is an embodiment wherein the at least one integrating optical element exhibits a ratio of the entry area for the excitation radiation to the exit area of 3 to 15 and in this situation the respective areas have the same aspect ratio. This feature serves to ensure that the half acceptance angle for the excitation source and the half exit angle of the useful light lies between 15° and 60°.

By preference, between the at least one excitation radiation source and the at least one integrating optical element is arranged an optical expansion device, in particular a diffusion element, for expanding the radiation emitted by the at least one excitation radiation source in a predefinable angular range. Through the use of an optical expansion device, the homogenization and mixing of the radiation by the integrating optical element are promoted on account of the multiple internal reflections enabled thereby in the integrable optical element.

By preference, the optical expansion device includes a lens, a mirror, a holographic element, a disk partially diffusing in the angular range, preferably a light shaping diffuser (LSD), or a volume phase grating. When a mirror is used, said mirror should be designed as small as possible in order to minimize the influence thereof on the useful light distribution. The use of a volume phase grating offers the advantage that such a grating is heavily wavelength- and angle-sensitive. The radiation emitted by the luminescent substance therefore remains uninfluenced by the volume phase grating when suitably designed. Particularly advantageous is an embodiment wherein for example a disk partially diffusing in the angular range, preferably a light shaping diffuser (LSD), is mounted directly on the mirror which is implemented as a passive reflector.

A further preferred embodiment is characterized in that at least the surface of the at least one heat sink, to which the at least one luminescent substance is thermally linked, is designed as reflective, having a reflection coefficient of at least 0.5, preferably at least 0.75, by particular preference at least 0.85, to radiation from the excitation radiation source and/or from the at least one luminescent substance on excitation by the radiation emitted by the excitation radiation source. This takes into consideration the fact that the converted radiation is emitted into the complete spatial angle as a result of excitation of the luminescent substance. As a result of such a reflective design of the heat sink, it is possible to utilize a maximum of said radiation as effective radiation. It is then also possible to design the thickness of the luminescent substance to be less, which enables a more efficient cooling.

Since embodiments are possible wherein non-converted portions of the excitation radiation are required in order to effect the composition of light of a desired color, it can moreover be helpful to design the heat sink as reflective to radiation from the excitation radiation source. In this situation it is sufficient to design the surface of the heat sink for a diffuse reflection. An extension of the optical path through the luminescent substance layer is moreover achieved as a result, which means that thinner luminescent substance layers are made possible. This further improves a light source unit according to the invention in respect of thermal considerations. If no superimposition of excitation radiation and converted radiation is required for the application, in other words the luminescent substance is configured in such a manner that a maximum conversion of the excitation radiation occurs, no reflective heat sink layer is required but only a sufficiently thick luminescent substance layer.

A light source unit according to the invention is particularly advantageous if it includes at least two excitation radiation sources, whereby the light source unit furthermore includes an optical collimating device for collimating the radiation emitted by the at least two excitation radiation sources. This utilizes the advantage that laser sources offer outstanding focusing and collimation capabilities on account of their small etendue. This means that laser light from many sources can be coupled in, as a result of which very high power densities can be achieved. In particularly advantageous fashion in this situation the laser sources can be positioned far apart from one another without suffering relevant losses. The result is that the laser sources are simple to cool. By contrast, the collimation and superimposition of the light from LEDs are not possible to the same extent. In spite of the laser sources being spaced apart from one another, according to the invention a very large amount of radiation can be collimated onto the comparatively small area of the at least one luminescent substance, which results in a high density of effective radiation. By particular preference, the optical collimating device includes at least one lens, one optical system or one fiber optic device.

By preference, the light source unit furthermore includes at least one mirror, whereby the at least one integrating optical element is coupled between the luminescent substance and the at least one mirror. Use of this mirror serves to ensure that the effective radiation is made available in a spatial angle which is different from the location from which the excitation radiation emanates. With regard to a first design, the at least one mirror is accordingly designed as a dichroic mirror which is transparent to the radiation from the excitation radiation source and reflective to radiation emitted by the at least one luminescent substance on excitation by the at least one excitation radiation source. Alternatively, the mirror can be designed as a dichroic mirror which is reflective to the radiation from the excitation radiation source and transparent to radiation emitted by the at least one luminescent substance on excitation by the at least one excitation radiation source.

In order to avoid the use of a dichroic mirror, provision can be made that the side of the mirror facing the at least one luminescent substance is designed to be reflective to radiation emitted by the at least one luminescent substance on excitation by the at least one excitation radiation source, whereby the mirror has an aperture, in particular an opening, for coupling radiation from the excitation radiation source into the integrating optical element. In preferred embodiments the diameter of the opening is approx. 0.5 to 2 mm, by particular preference approx. 1 mm. As already mentioned, the mirror can also be designed as a passive reflector which is reflective to radiation from the excitation radiation source. Such a mirror should be implemented with the smallest possible dimensions in order that its influence on the effective radiation remains negligible.

By particular preference, the integrating optical element is immersively linked to the at least one luminescent substance. This means that the connection between integrating optical element and the luminescent substance is implemented either without an air gap or is effected by means of a material having a matched refractive index. In either case this means that almost the entire excitation radiation exiting the integrating optical element can be utilized for excitation of the luminescent substance and conversely the entire effective radiation emitted by the luminescent substance, either with or without conversion, depending on the application, enters the integrating optical element and is thus available for the application.

By preference, the light source unit includes at least one first and one second luminescent substance, whereby the first luminescent substance is designed to emit radiation in a first wavelength range on excitation by the at least one excitation radiation source, whereby the second luminescent substance is designed to emit radiation in a second wavelength range different from the first wavelength range on excitation by the at least one excitation radiation source. In particular, when a light source unit according to the invention is used in projection applications, the production of multi-color images is made possible by this means. In this situation, the first and the second luminescent substance can be applied mixed with one another onto the at least one heat sink. By using appropriate filter devices in the optical path of the effective radiation both colors, although they are produced by spatial mixing, can be made available sequentially for subsequent applications.

Alternatively, the first and the second luminescent substances can be applied spatially separated on the at least one heat sink, for example in the form of a checkerboard pattern. In this context, it is preferred if the at least one heat sink is mounted in movable fashion, whereby the light source unit furthermore includes a moving device for moving the at least one heat sink which means that, depending on the movement of the at least one heat sink, during a first period of time the first luminescent substance and during a second period of time the second luminescent substance is exposed to the radiation from the at least one excitation radiation source. As a result of this measure, light of a differing wavelength can be generated sequentially when using a single excitation radiation source, which is desirable in particular in respect of projection applications. In this situation, the at least one heat sink can be mounted such that it can be rotated, whereby different luminescent substances are exposed to the radiation from the excitation source as a result of rotation of the heat sink. An additional cooling effect can be achieved as a result of the rotatable mounting of the heat sink. As an alternative to the rotatable mounting, the at least one heat sink can be mounted to be capable of translatory motion in order to achieve the same goal. The translatory motion is effected particularly advantageously through the use of a linear motor. As an alternative to a movable heat sink, radiation from the excitation source can be directed sequentially onto the spatially separated luminescent substances, preferably using an optical system designed for the purpose.

Finally, provision can be made that the light source unit furthermore includes an optical system which is designed to direct the radiation from the excitation radiation source in such a manner that, in the case of a fixed heat sink, during a first period of time the first luminescent substance and during a second period of time the second luminescent substance is exposed to the radiation from the at least one excitation radiation source.

The preferred embodiments presented with reference to a light source unit according to the invention and their advantages apply accordingly, insofar as applicable, to a projector according to the invention which includes a light source unit according to the invention.

BRIEF DESCRIPTION OF THE DRAWINGS

Exemplary embodiments of the present invention will be described in detail in the following with reference to the attached drawings. In the drawings.

DETAILED DESCRIPTION

Figure 1:
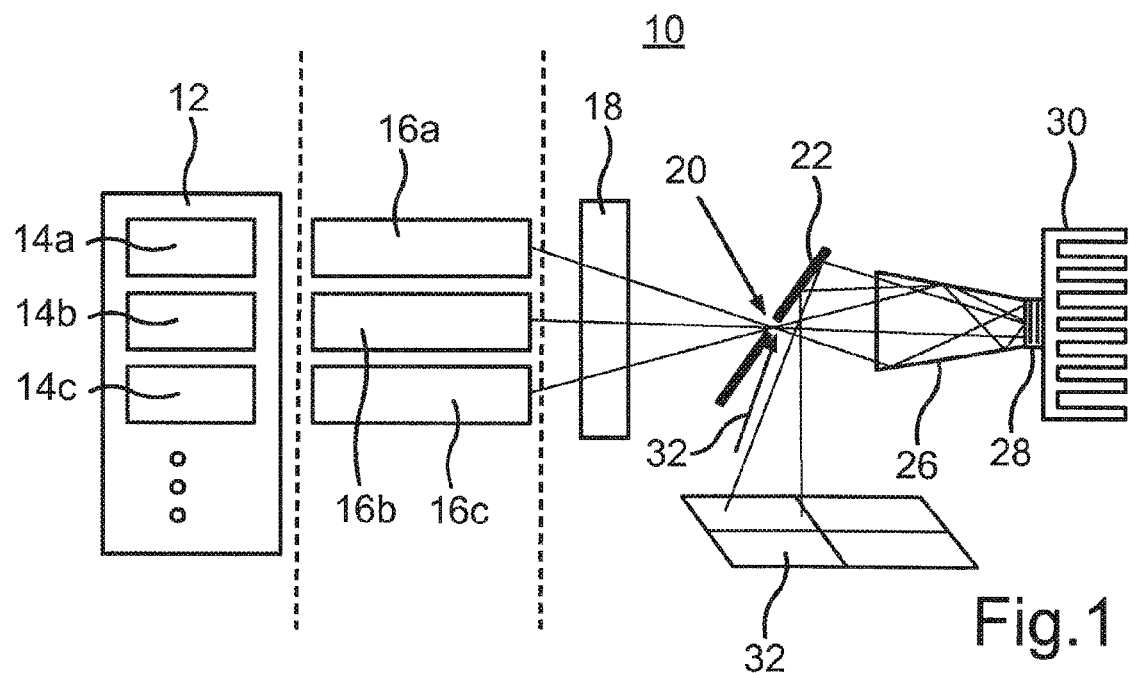
FIG. 1 shows a schematic view of a first exemplary embodiment of a light source unit according to the invention.

In the different embodiments presented in the following the same reference characters are used for the same elements or elements having the same function. For the sake of clarity, said reference characters are introduced only once.

FIG. 1 shows a schematic view of a first exemplary embodiment of a light source unit 10 according to the invention. This includes a laser array 12 having a multiplicity of laser sources 14a, 14b, 14c, each of which includes at least one laser diode. Associated with each laser source 14a to 14c is an optical system 16a to 16c, by means of which the angular distribution of the light emitted by the respective laser source 14a to 14c can be influenced for example for the purpose of focusing. There follows in the optical path an optical collimating device 18 which serves to focus the light from the laser sources 14a to 14c onto an opening 20 in a dichroic mirror 22. The mirror is tilted by a predefinable angle with respect to the optical path, for example by 45°. In the opening 20 is arranged a diffusion disk 24 which results in an expansion of the radiation passing through the opening 20. The diffusion disk 24 can be implemented for example as an LSD (light shaping diffuser). The expanded radiation enters an integrating optical element 26, the end of which is immersively coupled with a luminescent substance 28 which is thermally linked to a heat sink 30. The integrating optical element 26 has a maximum acceptance angle. Radiation which enters the integrating optical element 26 at a greater angle does not reach the luminescent substance 28. The collimating device 18 is designed in such a manner that the angular distribution of the radiation is less than or equal to the permissible entry distribution of the integrating optical element 26 after passing through the opening 20 and the diffusion disk 24. The integrating optical element 26 is designed and arranged with respect to the optical path of the radiation from the laser sources in such a manner that at least a part of the radiation emitted by the laser sources 14a to 14c entering in the acceptance angle range of the integrating optical element 26 is subjected to at least one internal reflection in the integrating optical element 26 before it exits the integrating optical element 26 again and strikes the at least one luminescent substance 28. By this means, a homogenization and mixing of the radiation striking the luminescent substance 28 is achieved.

In this context, the cross-section of the at least one integrating optical element 26 is designed to be not rotationally symmetrical, preferably angular, by particular preference rectangular.

The footprint and the volume of the luminescent substance 28 are formed in such a manner that a radiation conversion into the desired light color is enabled. The volume is optimized with regard to a minimum thermal resistance. In this situation, the volume is chosen in consideration of the heat to be dissipated and the capacity of the heat sink such that the temperature in the luminescent substance is below 200° C.

If the surface of the heat sink 30 is designed to be reflective to excitation radiation, the optical path length of the excitation radiation in the luminescent substance 28 can be extended because it passes through the luminescent substance 28 twice, namely once on the way in and once on the way back out after being reflected. This means that the luminescent substance volume can be reduced again, which results in a significantly improved thermal behavior.

The integrating optical element 26 serves to ensure that the intensity of the excitation radiation on the luminescent substance 28 is distributed extremely homogeneously and that no local increases in intensity, so-called hot spots, thus occur which would result in a degradation, oversaturation and reduction in efficiency of the luminescent substance 28. Furthermore, the thermal distribution and thus the efficiency of the cooling are improved by this means.

With the excitation of the luminescent substance 28 by the excitation radiation which is homogenized and adapted to the footprint of the luminescent substance 28, depending on the design of the luminescent substance 28 as a combination of chemical composition and volume characteristic, said excitation radiation is converted into radiation of a desired light color, characterized by the spectrum or intensity, and color coordinates, thereof. The excited luminescent substance 28 emits the converted radiation in Lambertian fashion. As a result of the reflective design of the heat sink 30, in particular implemented by means of a silvering between heat sink 30 and luminescent substance 28, the converted radiation is coupled in Lambertian fashion into the exit side of the integrating optical element 26. The integrating optical element 26 then functions as an integrating collecting optical system for the converted effective radiation which now strikes the mirror 22 in the angular distribution predetermined thereby and is directed thereby onto a homogeneously illuminated field 32 of output radiation.

With the light source unit 10 according to the invention illustrated in FIG. 1, a homogeneous excitation of the luminescent substance 28 with the highest power density is achieved. With the aforementioned homogenization, the entire luminescent substance volume is excited under heaviest load conditions, limited by cooling, saturation effects or damage thresholds, and a highly efficient conversion can take place. This means that the maximum possible luminance can be achieved using the basic principle of the luminescent substance conversion of laser radiation.

If the luminescent substance layer is chosen to be sufficiently thick, no reflective layer is required between luminescent substance 28 and heat sink 30. Sufficiently thick here denotes a layer thickness, the transmissivity of which is less than 1%. With the available luminescent substances, the layer thickness required for this purpose is approximately 100 μm or less. Such a layer has sufficiently good thermal conductivity so as not to impede heat dissipation to the heat sink 30. With regard to such a layer, the ratio of absorbed excitation radiation to emitted conversion radiation depends exclusively on the material parameters of the luminescent substance 28, in particular absorption and particle size. No color coordinates variations will be experienced as a result of varying layer thicknesses, as is the case with all transmissive approaches.

Instead of a collecting lens as an example of an optical collimating device 18, it is also possible to use a fiber optic device. To this end, the optical systems 16a, 16c each include fiber couplers and the optical collimating device 18 includes optics for bringing together the fiber bundles.

In one preferred embodiment, three laser sources 14a to 14c are provided, whereby one of the laser sources delivers a red light and the two other sources deliver an excitation radiation having a wavelength which after conversion by the luminescent substance 28 results in blue and green light respectively. In this situation, the luminescent substance 28 is designed such that it does not convert red light. Spectral components of the three colors red, green and blue are therefore present in the effective radiation, and can be utilized sequentially by means of appropriate filtering, whereby the blue and the green spectral components have been obtained through conversion, the red spectral component through reflection.

Figure 2:
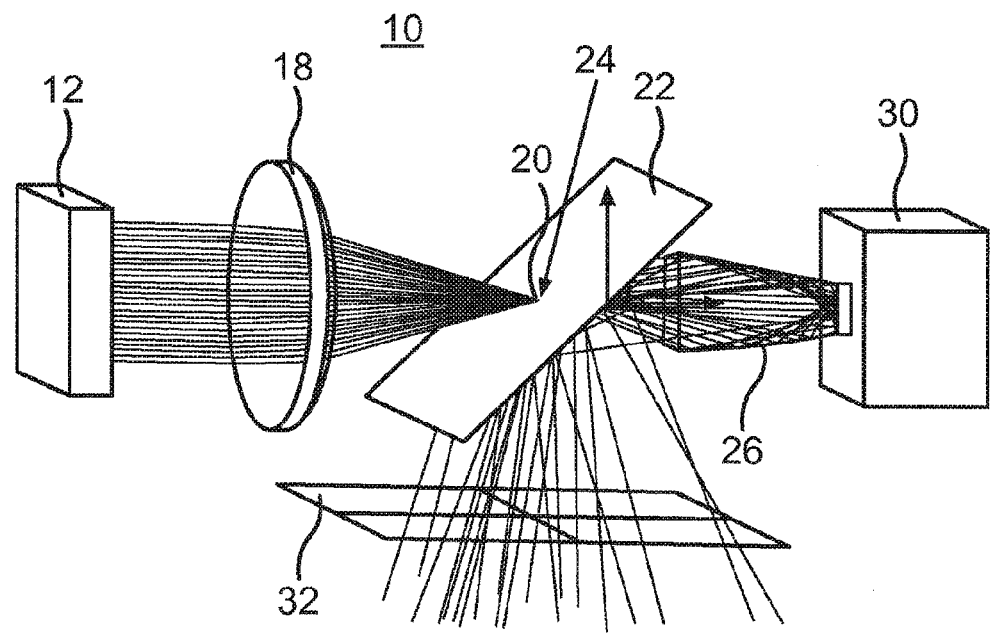
FIG. 2 shows a perspective view of an exemplary embodiment similar to that shown in FIG. 1.

FIG. 2 shows a perspective view of a light source unit 10 according to the invention, which is essentially the same as that illustrated in FIG. 1. It can be seen in this illustration that the cross-section of the integrating optical element 26 in this exemplary embodiment is designed as rectangular.

Figure 3:
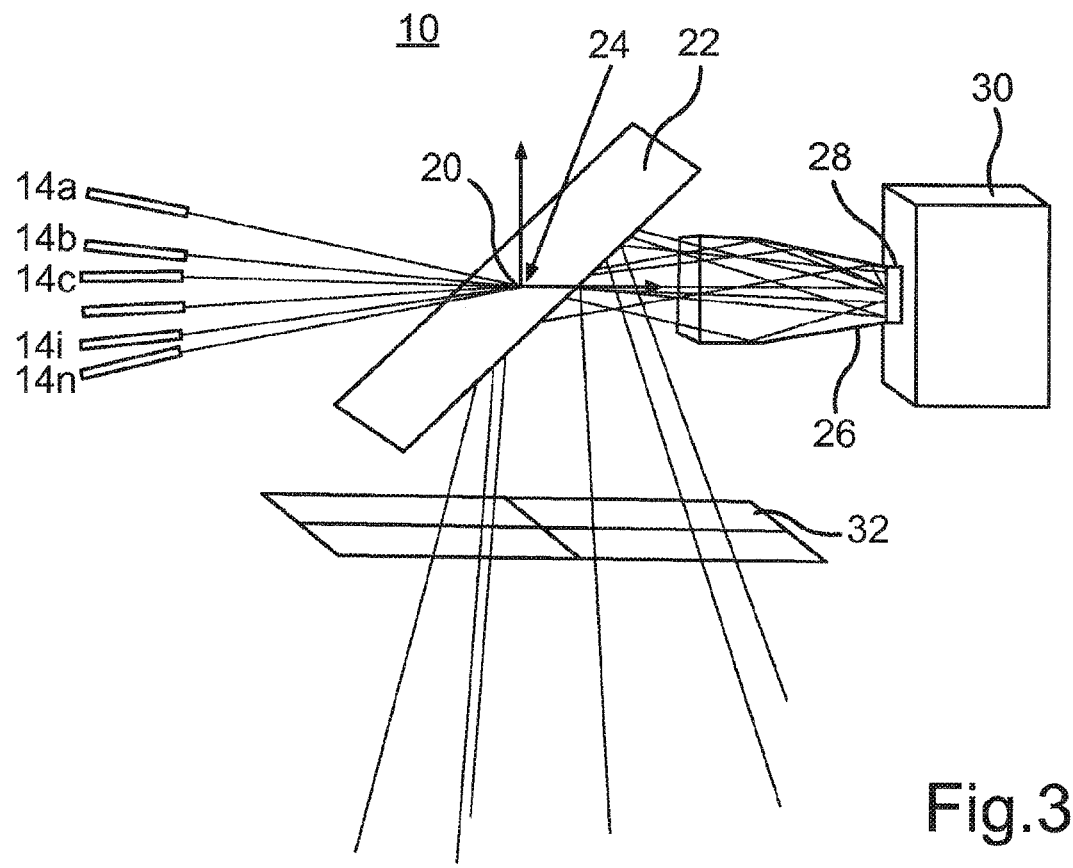
FIG. 3 shows a schematic view of a second exemplary embodiment of a light source unit according to the invention.

In the exemplary embodiment of a light source unit 10 according to the invention illustrated in FIG. 3 the laser sources 14a to 14n are directed directly onto the aperture 20 in the mirror 22 without a collecting optical system. The maximum angle of incidence is determined by the design of the integrating optical element 26.

Figure 4:
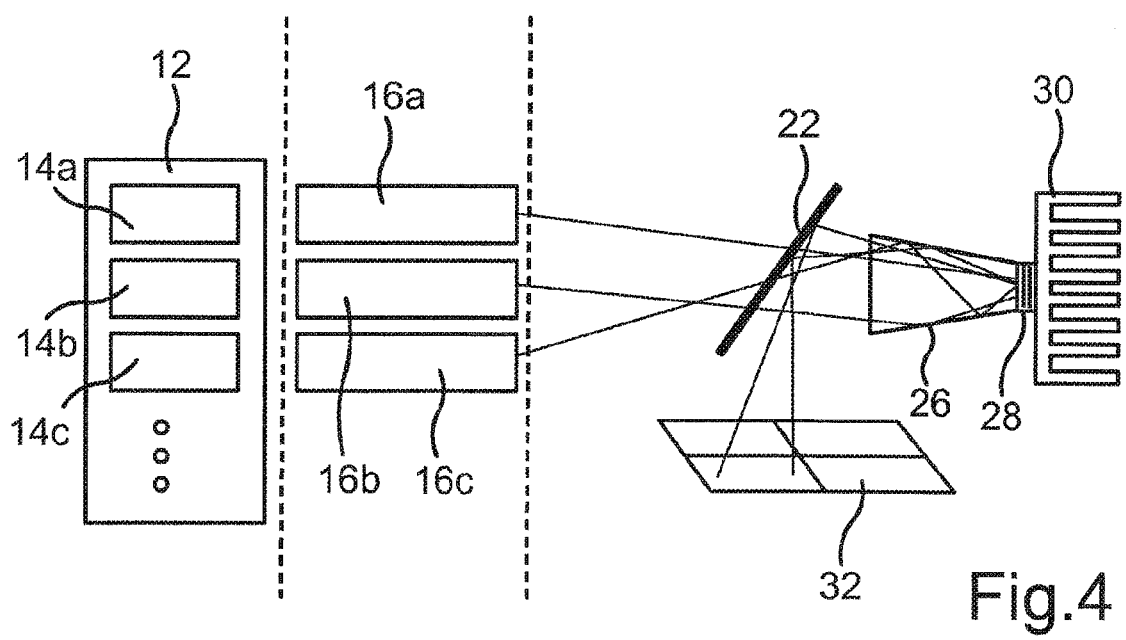
FIG. 4 shows a schematic view of a third exemplary embodiment of a light source unit according to the invention.

In the embodiment illustrated in FIG. 4 the mirror 22 is implemented as a dichroic mirror which is transparent to radiation from the laser sources 14a to 14c and reflective to the converted radiation emitted by the luminescent substance 28. As can be clearly seen in the diagram, both a part of the excitation radiation and also a part of the converted radiation are subjected to at least one internal reflection in the integrating optical element 26.

Figure 5:
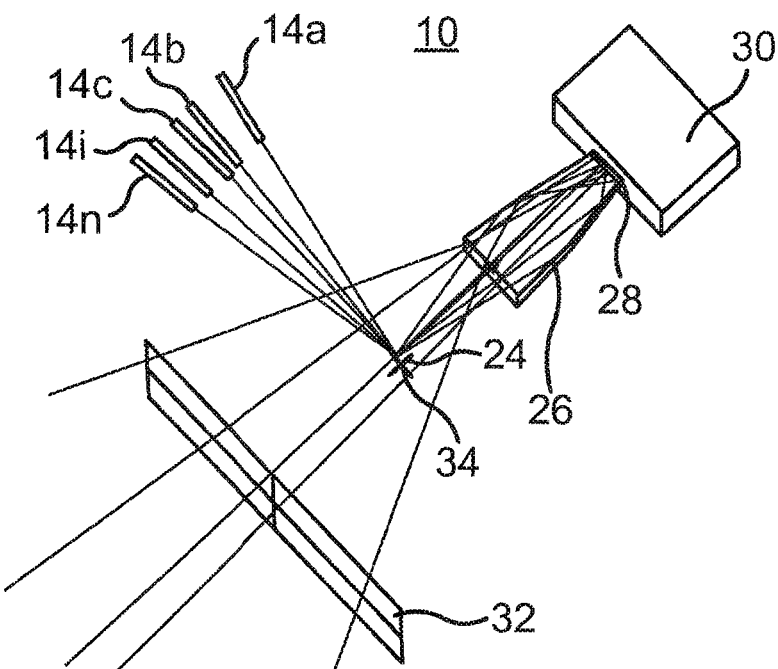
FIG. 5 shows a schematic view of a fourth exemplary embodiment of a light source unit according to the invention.

The embodiment of a light source unit 10 according to the invention illustrated in FIG. 5 does without a mirror for the effective radiation. For coupling the excitation radiation into the integrating optical element 26 at a permissible angular distribution a very small passive reflector 34 is used which can where applicable be curved in design. Just like the opening 20 in the embodiments according to FIGS. 1 to 3, on account of its size the mirror 34 has no significant influence on the distribution of the effective radiation. The use of a passive reflector having very small dimensions is made possible by the good focusability of the laser sources used for the excitation.

Instead of the mirror 34, a holographic element or a volume phase grating can also be used at this point. In this situation, a volume phase grating is heavily wavelength and angle selective, which means that the light converted by the luminescent substance 28 remains virtually unaffected thereby.

Whereas a diffusion disk 24 was used as the expansion device in the embodiments according to FIGS. 1 to 3, in the embodiment illustrated in FIG. 5 a diffusion device 24 is mounted directly on the passive reflector 34. A preferred embodiment of a diffusion element 24 delivers a Gaussian diffusion in 5°. In the embodiment illustrated in FIG. 4, a diffusion element 24 can be placed directly upstream of the mirror 22 for further expansion of the optical path.

Figure 6:
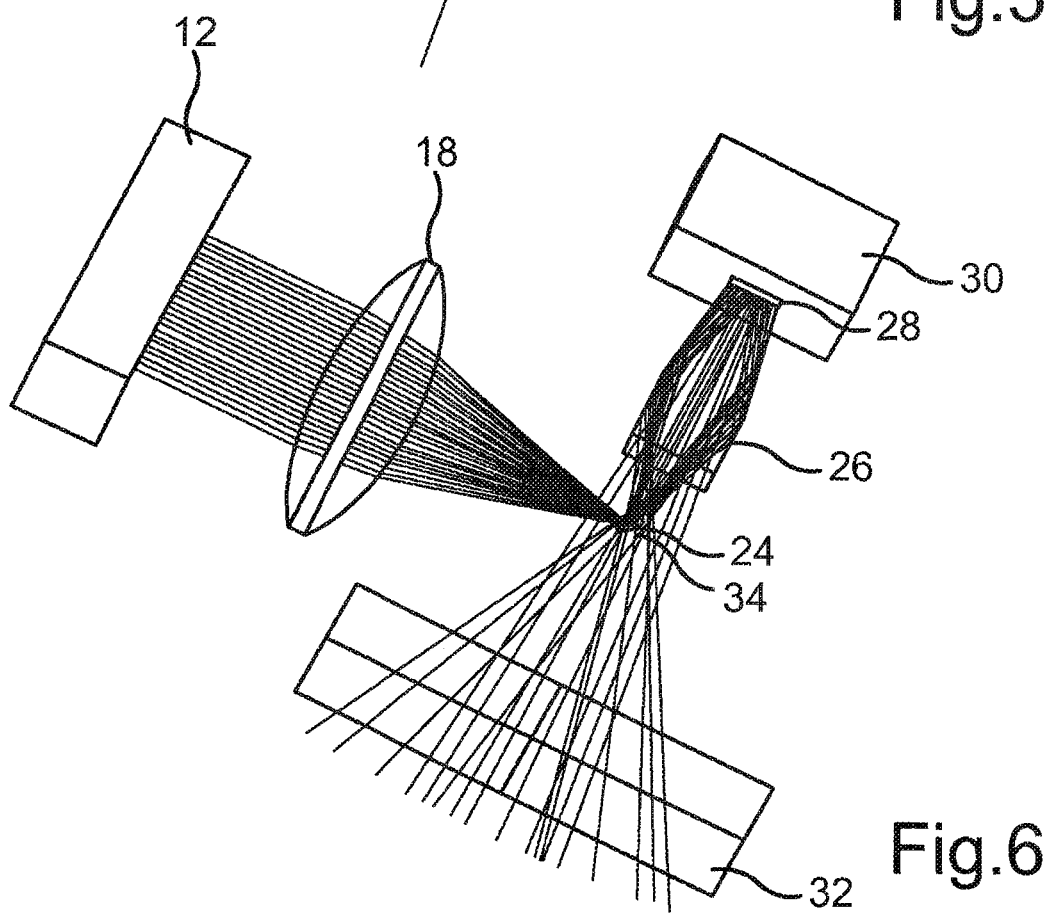
FIG. 6 shows a schematic view of a fifth exemplary embodiment of a light source unit according to the invention.

The embodiment illustrated in FIG. 6 differs from that illustrated in FIG. 5 in that a laser diode array is used for excitation purposes, whereby the radiation from the laser diodes is focused by means of a collecting optical system, cf. FIG. 2, onto the passive reflector 34.

In a preferred embodiment, the laser sources 14 are arranged in a 1-D array 12 such that the cross-section of the integrating optical element 26 is tilted diagonally with respect to the laser array 12.

By preference, such a light source unit 10 is employed in a projector or in a device for fiber coupling, in particular in an endoscope.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A light source unit, comprising: at least one cooling device;
at least one luminescent substance; at least one excitation radiation source having a laser source; and at least one optical element which is arranged between the at least one excitation radiation source and the at least one luminescent substance; wherein the at least one cooling device constitutes a heat sink, wherein the at least one luminescent substance is linked thermally to the at least one heat sink; and wherein the optical element is designed as an integrating optical element and is coupled between the at least one excitation radiation source and the at least one luminescent substance in such a manner that at least a part of the radiation emitted by the at least one excitation radiation source, entering in an acceptance angle range of the integrating optical element, is subjected to at least one internal reflection in the integrating optical element before it exits the integrating optical element and strikes the at least one luminescent substance, and that at least a part of the radiation emitted by the at least one luminescent substance enters the integrating optical element and exits the integrating optical element as effective radiation,
wherein at least the surface of the at least one heat sink, to which the at least one luminescent substance is thermally linked, is designed as reflective having a reflection coefficient of at least 0.5, to radiation at least one of from the excitation radiation source and from the at least one luminescent substance on excitation by the radiation emitted by the excitation radiation source.

2. The light source unit as claimed in claim 1, wherein the integrating optical element is furthermore designed in such a manner that at least a part of the radiation emitted by the at least one luminescent substance, entering the integrating optical element, is subjected to at least one internal reflection in the integrating optical element before it exits the integrating optical element.

3. The light source unit as claimed in claim 1, wherein the cross-section of the at least one integrating optical element is designed as not rotationally symmetrical.

4. The light source unit as claimed in claim 1, wherein between the at least one excitation radiation source and the at least one integrating optical element is arranged an optical expansion device for expanding the radiation emitted by the at least one excitation radiation source in a predefinable angular range.

5. The light source unit as claimed in claim 4, wherein the optical expansion device comprises an element selected from a group consisting of: a lens; a mirror; a holographic element; a disk partially diffusing in the angular range; and a volume phase grating.

6. The light source unit as claimed in claim 1, wherein it comprises at least two excitation radiation sources, whereby the light source unit furthermore comprises an optical collimating device for collimating the radiation emitted by the at least two excitation radiation sources.

7. The light source unit as claimed in claim 6, wherein the optical collimating device comprises at least one element selected from a group consisting of: a lens; one optical system; and one fiber optic device.

8. The light source unit as claimed in claim 1, wherein the light source unit comprises at least one mirror, whereby the at least one integrating optical element is coupled between the luminescent substance and the at least one mirror.

9. The light source unit as claimed in claim 8, wherein the at least one mirror is designed as a dichroic mirror which is transparent to the radiation from the excitation radiation source and reflective to radiation emitted by the at least one luminescent substance on excitation by the at least one excitation radiation source, or vice versa.

10. The light source unit as claimed in claim 8, wherein the side of the mirror facing the at least one luminescent substance is designed to be reflective to radiation emitted by the at least one luminescent substance on excitation by the at least one excitation radiation source, whereby the mirror has an opening for coupling radiation from the excitation radiation source into the integrating optical element.

11. The light source unit as claimed in claim 1, wherein the integrating optical element is immersively linked to the at least one luminescent substance.

12. The light source unit as claimed in claim 1, wherein the light source unit comprises at least one first and one second luminescent substance, wherein the first luminescent substance is designed to emit radiation at a first wavelength on excitation by the at least one excitation radiation source, wherein the second luminescent substance is designed to emit radiation at a second wavelength different from the first wavelength on excitation by the at least one excitation radiation source.

13. The light source unit as claimed in claim 12, wherein the first and the second luminescent substance, mixed with one another, are thermally linked to the at least one heat sink.

14. The light source unit as claimed in claim 12, wherein the first and the second luminescent substance, spatially separated, are thermally linked to the at least one heat sink.

15. The light source unit as claimed in claim 14, wherein the at least one heat sink is mounted in movable fashion, wherein the light source unit furthermore comprises a moving device for moving the at least one heat sink which means that, depending on the movement of the at least one heat sink, during a first period of time the first luminescent substance and during a second period of time the second luminescent substance is exposed to the radiation from the at least one excitation radiation source.

16. The light source unit as claimed in claim 14, wherein the light source unit furthermore comprises an optical system which is designed to direct the radiation from the excitation radiation source in such a manner that, in the case of a fixed heat sink, during a first period of time the first luminescent substance and during a second period of time the second luminescent substance is exposed to the radiation from the at least one excitation radiation source.

17. A projector, comprising: a light source unit, comprising: at least one cooling device; at least one luminescent substance; at least one excitation radiation source having a laser source; and at least one optical element which is arranged between the at least one excitation radiation source and the at least one luminescent substance; wherein the at least one cooling device constitutes a heat sink, wherein the at least one luminescent substance is linked thermally to the at least one heat sink; and wherein the optical element is designed as an integrating optical element and is coupled between the at least one excitation radiation source and the at least one luminescent substance in such a manner that at least a part of the radiation emitted by the at least one excitation radiation source, entering in an acceptance angle range of the integrating optical element, is subjected to at least one internal reflection in the integrating optical element before it exits the integrating optical element and strikes the at least one luminescent substance, and that at least a part of the radiation emitted by the at least one luminescent substance enters the integrating optical element and exits the integrating optical element as effective radiation, wherein at least the surface of the at least one heat sink, to which the at least ne luminescent substance is thermally linked, is designed as reflective having a reflection coefficient of at least 0.5, to radiation at least one of from the excitation radiation source and from the at least one luminescent substance on excitation by the radiation emitted by the excitation radiation source.

18. A device for fiber coupling, comprising: a light source unit, comprising: at least one cooling device; at least one luminescent substance; at least one excitation radiation source having a laser source; and at least one optical element which is arranged between the at least one excitation radiation source and the at least one luminescent substance; wherein the at least one cooling device constitutes a heat sink, wherein the at least one luminescent substance is linked thermally to the at least one heat sink; and wherein the optical element is designed as an integrating optical element and is coupled between the at least one excitation radiation source and the at least one luminescent substance in such a manner that at least a part of the radiation emitted by the at least one excitation radiation source, entering in an acceptance angle range of the integrating optical element, is subjected to at least one internal reflection in the integrating optical element before it exits the integrating optical element and strikes the at least one luminescent substance, and that at least a part of the radiation emitted by the at least one luminescent substance enters the integrating optical element and exits the integrating optical element as effective radiation, wherein at least the surface of the at least one heat sink, to which the at least one luminescent substance is thermally linked, is designed as reflective having a reflection coefficient of at least 0.5, to radiation at least one of from the excitation radiation source and from the at least one luminescent substance on excitation by the radiation emitted by the excitation radiation source.

19. The device as claimed in claim 18, configured as an endoscope.

* * * * *